(12) United States Patent
Fleury et al.

(10) Patent No.: US 7,919,100 B2
(45) Date of Patent: Apr. 5, 2011

(54) SOLUBLE AND STABILIZED TRIMERIC FORM OF GP41 POLYPEPTIDES

(75) Inventors: Sylvain Fleury, Lausanne (CH); Marc P Girard, Lyons (FR); Marie-Gaëlle Roger, Grenoble (FR); Nicolas Mouz, Grenoble (FR); Pierre-François Serres, Saint-Genis Laval (FR)

(73) Assignee: Mymetics Corporation, New York, NY (US)

( * ) Notice: Subject to any disclaimer, the term of this patent is extended or adjusted under 35 U.S.C. 154(b) by 842 days.

(21) Appl. No.: 10/573,704

(22) PCT Filed: Jul. 29, 2004

(86) PCT No.: PCT/IB2004/002433
§ 371 (c)(1),
(2), (4) Date: Feb. 27, 2007

(87) PCT Pub. No.: WO2005/010033
PCT Pub. Date: Feb. 3, 2005

(65) Prior Publication Data
US 2008/0213292 A1    Sep. 4, 2008

Related U.S. Application Data

(60) Provisional application No. 60/490,946, filed on Jul. 30, 2003.

(51) Int. Cl.
*A61K 39/21*    (2006.01)
(52) U.S. Cl. .................................. 424/188.1; 424/208.1
(58) Field of Classification Search ......................... None
See application file for complete search history.

(56) References Cited

U.S. PATENT DOCUMENTS
6,455,265 B1    9/2002    Serres

FOREIGN PATENT DOCUMENTS
WO    WO 99/25377 A1    5/1999
WO    WO 02/34909 A2    5/2002

OTHER PUBLICATIONS

Desrosiers, R. C., 2004, Prospects for an AIDS vaccine, Nat. Med. 10(3):221-223.*
Gallo, R. C., 2005, The end or the beginning of the drive to an HIV-preventive vaccine: a view from over 20 years, The Lancet 366:1894-1898.*
Burton, D. R., et al., 2004, HIV vaccine design and the neutralizing antibody problem, Nat. Immunol. 5(3):233-236.*
Walker, B. D., and D. R. Burton, 2008, Toward an AIDS vaccine, Science 320:760-765.*
Louis J M, et al; (2001); "Design and Properties of Nccg-gp41, a Chimeric gp41 Molecule with Nanomolar HIV Fusion Inhibitory Activity"; Journal of Biological Chemistry; vol. (276); pp. 29485-29489.
Eckert D M, et al; (2001); "Design of Potent Inhibitors of HIV-1 Entry From the gp41 N-peptide Region"; Proceedings of the National Academy of Science of USA; vol. (98); pp. 11187-11192.
Root M J, et al; (2001); "Protein Design of an HIV-1 Entry Inhibitor"; Science; vol. (291); pp. 884-888.
Lu M, et al; (1999); "Subdomain Folding and Biological Activity of the Core Structure from Human Immunodeficiency Virus Type 1 gp41: Implications for Viral Membrane Fusion"; Journal of Virology; vol. (73); pp. 4433-4438.
Serres P F; (2001); "AIDS: an Immune Response Against the Immune System. Role of a Precise Tridimensional Molecular Mimicry"; Journal of Autoimmunity; vol. (16); pp. 287-291.

* cited by examiner

*Primary Examiner* — Jeffrey S. Parkin
(74) *Attorney, Agent, or Firm* — Oliff & Berridge, PLC

(57) ABSTRACT

The present invention concerns a modified polypeptide containing at least an immunodominant region and the connecting loop between N- and C-helices of gp41 ectodomain of HIV-1, wherein the connecting loop includes at least a linker fragment having: —a size convenient for keeping the native conformation of the interaction between N- and C-helices, and —an hydrophily sufficient to provide a soluble and stable trimeric form to said modified polypeptide.

6 Claims, 8 Drawing Sheets

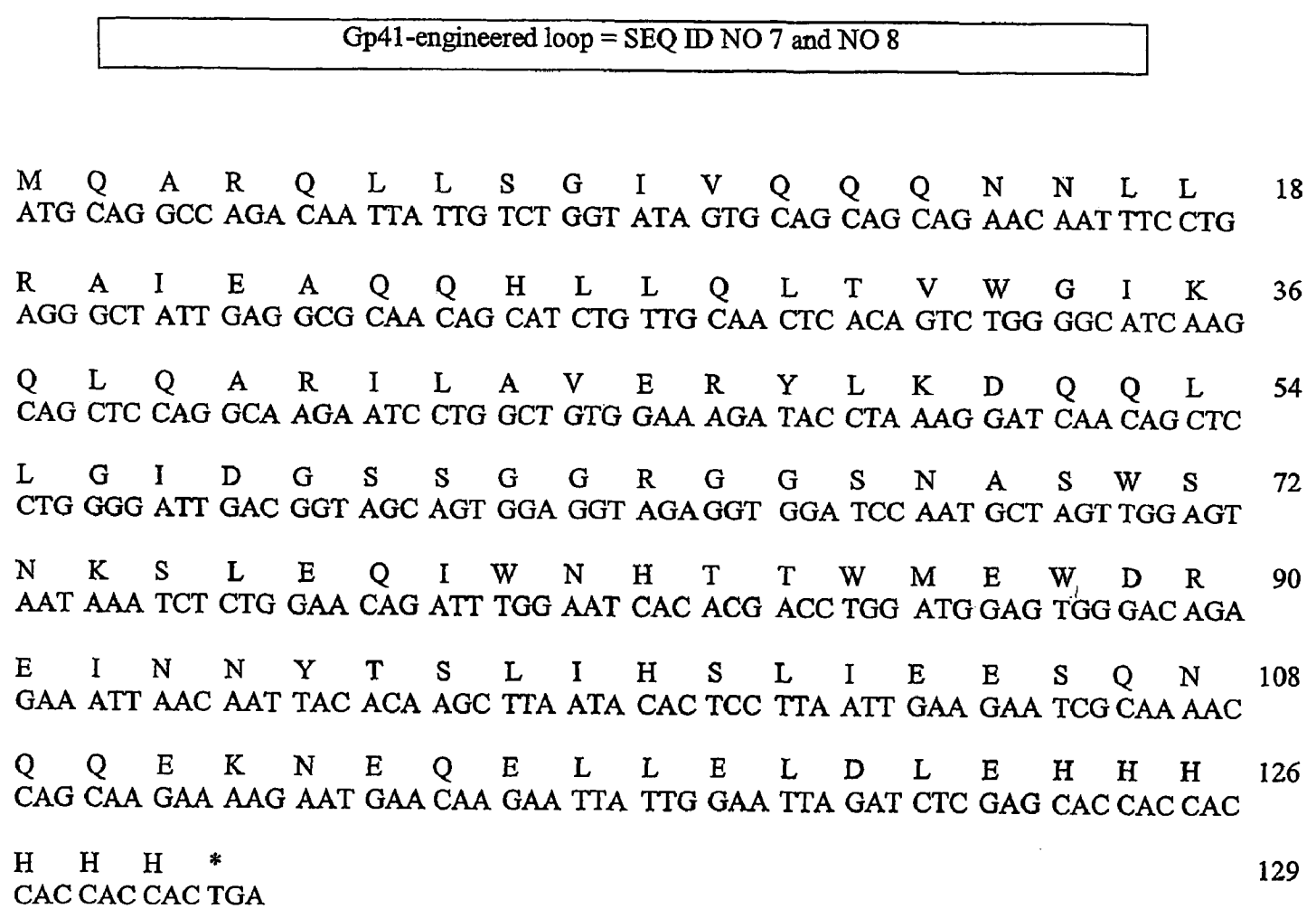

Gp41-engineered loop = SEQ ID NO 7 and NO 8

```
  M   Q   A   R   Q   L   L   S   G

2A

Gp41 (region 540-679): SEQ ID NO 1

QARQLLSGIVQQQNNLLRAIEAQQHLLQLTVWGIK
QLQARILAVERYLKDQQLLGIWGCSGKLICTTAVP
WNASWSNKSLEQIWNNMTWMEWDREINNYTSLIHS
LIEESQNQQEKNEQELLELDKWASLWNWFNITNWL

2B

Gp41 regions

| Region 550-572 | SEQ ID NO 3 | QQQNNLLRAIEAQQHLLQLTVWG |
| Region 567-596 | SEQ ID NO 4 | QLTVWGIKQLQARILAVERYLKDQQLLGIW |
| Region 585-615 | SEQ ID NO 5 | RYLKDQQLLGIWGCSGKLICTTAVPWNASWS |
| Region 623-658 | SEQ ID NO 6 | WNNMTWMEWDREINNYTSLIHSLIEESQNQQEKNEQ |

2C

Linker oligopeptide: SEQ ID NO 2

S G G R G G S

2D

Region 599-610: SEQ ID NO 15 :    S G K L I C T T A V P W (-12 residues)

Region 593-617: SEQ ID NO 16:  L G I W G C S G K L I C T T A V P W N A S W S N K (-25 residues)

FIGURE 2

SEQ ID NO 13 and 14 (GP41 matrix):

```
(V)  Q540 A    R    Q    L

SEQ ID NO 17

| M | Q | A | R | Q | L | L | S | G | I | V | Q | Q | Q | N | N | L | L | 18 |
| R | A | I | E | A | Q | Q | H | L | L | Q | L | T | V | W | G | I | K | 36 |
| Q | L | Q | A | R | I | L | A | V | E | R | Y | L | K | D | Q | Q | L | 54 |
| S | G | G | R | G | G | S | S | L | E | Q | I | W | N | H | T | T | W | 72 |
| M | E | W | D | R | E | I | N | N | Y | T | S | L | I | H | S | L | I | 90 |
| E | E | S | Q | N | Q | Q | E | K | N | E | Q | E | L | L | E | L | D | 108 |
| K | W | A | S | L | W | N | W | F | N | I | T | N | W | L | D | H | H | 126 |
| H | H | H | H | | | | | | | | | | | | | | | |

FIGURE 4A

SEQ ID NO 18

| M | Q | A | R | Q | L | L | S | G | I | V | Q | Q | Q | N | N | L | L | 18 |
| R | A | I | E | A | Q | Q | H | L | L | Q | L | T | V | W | G | I | K | 36 |
| Q | L | Q | A | R | I | L | A | V | E | R | Y | L | K | D | Q | Q | L | 54 |
| S | G | G | R | G | G | S | S | L | E | Q | I | W | N | H | T | T | W | 72 |
| M | E | W | D | R | E | I | N | N | Y | T | S | L | I | H | S | L | I | 90 |
| E | E | S | Q | N | Q | Q | E | K | N | E | Q | E | L | L | E | L | D | 108 |
| K | W | A | S | L | W | N | W | F | N | I | T | N | D | H | H | H | H | 126 |
| H | H | | | | | | | | | | | | | | | | | |

FIGURE 4B

SEQ ID NO 19

| M | Q | A | R | Q | L | L | S | G | I | V | Q | Q | Q | N | N | L | L | 18 |
|---|---|---|---|---|---|---|---|---|---|---|---|---|---|---|---|---|---|---|
| R | A | I | E | A | Q | Q | H | L | L | Q | L | T | V | W | G | I | K | 36 |
| Q | L | Q | A | R | I | L | A | V | E | R | Y | L | K | D | Q | Q | L | 54 |
| L | G | I | W | G | S | S | G | G | R | G | G | S | S | L | E | Q | I | 72 |
| W | N | H | T | T | W | M | E | W | D | R | E | I | N | N | Y | T | S | 90 |
| L | I | H | S | L | I | E | E | S | Q | N | Q | Q | E | K | N | E | Q | 108 |
| E | L | L | E | L | D | K | W | A | S | L | W | N | W | F | N | I | T | 126 |
| N | W | L | D | H | H | H | H | H | H |   |   |   |   |   |   |   |   | 136 |

FIGURE 5A

SEQ ID NO 20

| M | Q | A | R | Q | L | L | S | G | I | V | Q | Q | Q | N | N | L | L | 18 |
|---|---|---|---|---|---|---|---|---|---|---|---|---|---|---|---|---|---|---|
| R | A | I | E | A | Q | Q | H | L | L | Q | L | T | V | W | G | I | K | 36 |
| Q | L | Q | A | R | I | L | A | V | E | R | Y | L | K | D | Q | Q | L | 54 |
| L | G | I | W | G | S | S | G | G | R | G | G | S | S | L | E | Q | I | 72 |
| W | N | H | T | T | W | M | E | W | D | R | E | I | N | N | Y | T | S | 90 |
| L | I | H | S | L | I | E | E | S | Q | N | Q | Q | E | K | N | E | Q | 108 |
| E | L | L | E | L | D | K | W | A | S | L | W | N | W | F | N | I | T | 126 |
| N | D | H | H | H | H | H | H |   |   |   |   |   |   |   |   |   |   | 134 |

FIGURE 5B

SEQ ID NO 21

|   |   |   |   |   |   |   |   |   |   |   |   |   | M | L | L | 3 |
|---|---|---|---|---|---|---|---|---|---|---|---|---|---|---|---|---|
| R | A | I | E | A | Q | Q | H | L | L | Q | L | T | V | W | G | I | K | 21 |
| Q | L | Q | A | R | I | L | A | V | E | R | Y | L | K | D | Q | Q | L | 39 |
| S | G | G | R | G | G | S | S | L | E | Q | I | W | N | H | T | T | W | 57 |
| M | E | W | D | R | E | I | N | N | Y | T | S | L | I | H | S | L | I | 75 |
| E | E | S | Q | N | Q | Q | E | K | N | E | Q | E | L | L | E | L | D | 93 |
| K | W | A | S | L | W | N | W | F | N | I | T | N | W | L | D | H | H | 111 |
| H | H | H | H |   |   |   |   |   |   |   |   |   |   |   |   |   |   | 115 |

FIGURE 6

SEQ ID NO 9 :  5' GG AAT CCA CAT ATG CAG GCC AGA CAA TTA TTG 3'

SEQ ID NO 10 : 5'ACC GTT GGA TCC ACC TCT ACC TCC ACT GCT ACC GTC AAT CCC CAG GAG CTG TTG ATC 3'

SEQ ID NO 11 : 5' GG AAT CCA GGA TCC AAT GCT AGT TGG AGT AAT AAA TCT CTG GAA 3'

SEQ ID NO 12 : 5' GCC CGG CTC GAG ATC TAA TTC AAT AAT TCT TGT TC ATT CTT TTC 3'

FIGURE 7

SOLUBLE AND STABILIZED TRIMERIC FORM OF GP41 POLYPEPTIDES

This application is a national stage application of International Application No. PCT/IB2004/002433, filed Jul. 29, 2004, which claims the benefit of U.S. Provisional Application No. 60/490,946, filed Jul. 30, 2003.

The instant invention is directed to soluble and stabilized trimeric forms of the envelope glycoprotein gp41 of HIV-1 and to their use as vaccine agent.

BACKGROUND

Human immunodeficiency virus type 1 (HIV-1) encodes a 160 kDa envelope glycoprotein (gp160) precursor, which is proteolytically cleaved into the exterior (gp120) and transmembrane (gp41) glycoproteins.

In the glycoprotein mature envelope, the gp120 glycoprotein remains associated with the gp41 ectodomain through a noncovalent interaction. The native HIV-1 envelope glycoproteins exist as trimers that consist of three gp120 and three gp41 subunits and is anchored in the viral or infected cell membrane by the gp41 transmembrane region.

It has been shown that the binding of gp120 to the CD4 receptor induces conformational changes that promote subsequent interaction with one of a number of chemokine receptors (CXCR4, CCR5 . . . ). These binding events trigger conformational changes in gp41. In particular, studies by X-ray crystallography and nuclear magnetic resonance indicate that the viral envelope glycoprotein gp41 exists in at least three conformations, a native conformation (spike), a prefusogenic metastable conformation which is converted to a thermostable fusogenic "three hairpin" conformation following a triggering event, such as binding of HIV virus particle to the membrane of target cells.

So, the binding of gp120 to cellular coreceptors induces the gp41 conversion of a prefusogic form to a fusogenic form.

The linear organization of the gp41 includes a fusion peptide, an ectodomain (a N-terminal coiled-coil, a disulfide-bonded loop region, and a C-terminal α-helical segment) and a transmembrane domain.

In the fusogenic six-helix bundle, three N-terminal helices form a trimeric coiled-coil, and three C-terminal helices pack in the reverse direction into three hydrophobic grooves on the surface of the coiled-coil. This helical-hairpin structure corresponds to the fusion-active conformation of gp41. Because the membrane anchor and the fusion peptide of the gp41 ectodomain are embedded in the viral and target cell membranes, respectively, the formation of the fusogenic hairpin structure results in the colocalization of the two membranes and thus overcomes the energy barrier for membrane fusion.

The envelope glycoproteins represent the only realistic viral target for vaccine-induced neutralizing antibody responses because they promote viral membrane fusion through receptor-mediated conformational change and they are expressed on the surface of both virions and infected cells. Monomeric HIV-1 gp120 and derivatives were initially considered to be principal vaccine candidates. However, HIV-1 gp120 is highly variable and has repeatedly proven to be an immunogen ineffective at eliciting neutralizing antibodies against clinical HIV-1 isolates. Few of the antibodies raised by gp120 monomers effectively bind assembled HIV-1 envelope glycoprotein trimers.

In contrast, gp41 is an extremely immunogenic glycoprotein, inducing antibodies in essentially all HIV-infected individuals.

SUMMARY

The ectodomain of gp41 is the most conserved region in HIV-1 envelope, which otherwise exhibits considerable genetic diversity even among closely related isolates.

Furthermore, the gp41 performs a critical role in maintaining the conformation and infectivity of the HIV virion.

The antibodies targeting the six-helix bundle (fusogenic form) and prehairpin (prefusogenic form) structures arrest fusion under certain conditions. Antibodies having access to prehairpin and six-helix bundles conformations of gp41 would be capable of inhibiting gp41-mediated fusion. Furthermore, the six-helix bundle is an extremely stable structure.

Those observations allow considering the gp41 six-helix, under a modified form or not, as an attractive target for drugs and vaccine development.

In U.S. Pat. No. 6,455,265, the inventors showed that some gp41 derivatives could be particularly efficient for obtaining vaccine for preventing the pathogenic effects related to a retroviral infection with the proviso that the corresponding polypeptides have epitopes having a modified antigenicity so as to obtain a differential immune response with respect to the viral envelope, and some self-proteins.

More precisely, they discovered that conserved and immunodominant regions of the retroviral envelope could be responsible for harmful autoimmune phenomena, particularly in the case of the gp41 retroviral envelope. The inventors have observed that certain immunodominant regions of the gp41 exhibit three-dimensional structural analogies and/or cross-reactivity with certain regions of a protein of the human immune system, and in particular IL-2.

Accordingly, they proposed modified polypeptides obtained by modifying the antigenicity of the concerned epitope of the envelope protein, in order to obtain a differential immune response with respect to the viral envelope protein and these proteins of the human immune system.

Generally, the gp41 can be produced in baculovirus or mammalian cells but the yield is lower than in *E. coli*. Furthermore, the glycosylation in baculovirus or mammalian cells is different from the glycosylation of human cells and is not necessary for the immunogenicity of the protein. Gp41 is in fact very immunogenic without glycosylation.

However, recombinant HIV ectodomain of gp41 produced in *Escherichia coli* forms insoluble precipitates (aggregates of gp41 trimeric form) at neutral pH.

The instant invention is more precisely directed to propose stabilized hydrosoluble forms of gp41 protein, in particular of gp41 protein derivatives and more particularly of derivatives as disclosed in U.S. Pat. No. 6,455,265.

Unexpectedly, the inventors have discovered that it was possible to decrease significantly the hydrophobicity of the loop, resulting in an improvement of the solubilisation of the recombinant HIV ectodomain of gp41, without altering its immunogenic reactivity.

Accordingly, within one aspect of the invention there is provided a modified polypeptide containing at least an immunodominant region and the connecting loop between N- and C-helices of gp41 ectodomain of HIV-1, wherein the connecting loop includes at least a linker fragment having:
  a size convenient for keeping the native conformation of the interaction between N- and C-helices, and
  an hydrophily sufficient to provide a soluble and stable trimeric form to said modified polypeptide.

BRIEF DESCRIPTION OF THE DRAWINGS

FIG. 1 represents a coding DNA sequence and corresponding polypeptide sequence according to the invention.

FIG. 2A represents amino acids 540 to 679 (SEQ ID NO:1) of the gp160 envelope protein of HIV. The sequence is taken from a consensus sequence of 32 strains in the Swissprot database and is identical with the sequence of isolate ENV_HV1BR (Swiss-Prot P03377).

FIG. 2B represents peptide sequences (SEQ ID NOs:3-6, their numbering corresponding to FIG. 2A) of regions where structural analogies or homologies with IL-2 are present.

FIG. 2C represents a linker oligopeptide (SEQ ID NO:2) convenient for linking the N- and C-terminal peptides of gp41 after removal of amino acids 599 to 610 or 593 to 617 of the gp160 envelope protein of HIV of FIG. 2A.

FIG. 2D represents oligopeptide sequences (SEQ ID NOs: 15 and 16, their numbering corresponding to FIG. 2A) that may be advantageously replaced by a linker in accordance with the invention.

FIG. 3 represents amino represents amino acids 540 to 675 (SEQ ID NO:14) and the corresponding nucleotide sequence (SEQ ID NO:13) of the gp160 envelope protein of HIV. The sequence is taken from the reference strain HxB2 gp41, where amino acids 598 and 604 have been replaced with serine.

FIGS. 4A and 4B represent sequences (SEQ ID NOs:17 and 18) of two representative polypeptides according to the invention.

FIGS. 5A and 5B represent sequences (SEQ ID NOs:19 and 20) of two representative polypeptides according to the invention.

FIG. 6 represents a polypeptide sequence (SEQ ID NO:21) illustrating the invention, with N-terminal truncation, and comprising the linker sequence of FIG. 2C (SEQ ID NO:2).

FIG. 7 represents the primer sequences used in the amplification of the gp41 N-helix and the introduction of the linker (SEQ ID NOs:9 and 10) and for the amplification of the C-helix (SEQ ID NOs:11 and 12).

DETAILED DESCRIPTION OF EMBODIMENTS

Figure 8:
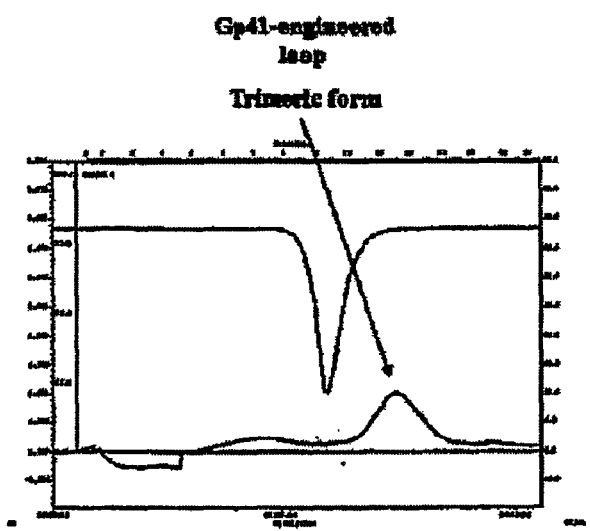
FIG. 8 is a chromatographic elution profile of the polypeptide of the invention on a Superdex 200 HR liquid chromatography column.

In the meaning of the instant invention, the expression "keeping the native conformation of the interaction between N- and C-helices" is understood to mean that the interaction between the N- and C-helices of the gp41-modified polypeptide is functionally similar or equivalent to the interaction of those helices of the wild-type gp41 polypeptide.

Within one embodiment of the invention, the linker fragment is included in the loop in substitution of all or only in part of a deleted wildtype oligopeptide.

Within another embodiment of the invention, the deleted wildtype oligopeptide is located in the region from 593 to 617, in particular in the region from 599 to 610 of the gp41 protein, according to the numbering of SEQ ID NO 1 in FIG. 2A.

Within another embodiment of the invention, the deleted oligopeptide is located in the region from 55 to 79, in particular in the region from 61 to 72, according to the numbering of SEQ ID NO 14 (FIG. 3).

Within a further embodiment, the deleted wild type oligopeptide consists of a sequence of at least 10, in particular 13 and more particularly 25 amino acid residues.

Within another embodiment, the linker fragment is an oligopeptide linker mainly based on hydrophilic amino acids residues.

Within still another embodiment of the invention, the oligopeptide linker consists of the sequence SGGRGGS as set forth in SEQ ID NO 2.

Within a second aspect of the invention, there is provided a polynucleotide encoding a modified polypeptide as disclosed above.

Within a third aspect of the invention, there is provided an expression vector comprising the following operably linked elements: a transcript promoter, a DNA segment encoding a modified polypeptide as disclosed above and a transcript terminator.

Within a fourth aspect of the invention, there is provided a vaccine for preventing the pathogenic effect related to a retroviral infection including as active material at least one modified polypeptide as disclosed above.

The definition given above implies that the polypeptide used comprises at least part of an immunodominant region of the gp41 viral envelope protein of HIV-1.

The modified polypeptide in accordance with the present invention may be, for example, the whole envelope protein of VIH-1, modified as indicated hereafter. The modified polypeptide may also be part of the envelope protein, modified as indicated hereafter, said part comprising at least one immunodominant fragment as defined hereafter. The modified polypeptide may also be a chimeric protein comprising at least part of the envelope protein, said part of the envelope protein being as defined above.

The peptide sequence 540 to 679 (SEQ ID NO:1), reproduced in FIG. 2A, is a gp41 consensus sequence of 32 HIV-1 strains in the Swiss Protein Database. This sequence is identical with the sequence of isolate ENV_HV1BR (Swiss-Prot P03377).

The peptide sequence 540 to 679 (SEQ ID NO:14), represented in FIG. 3, is derived from the HxB2 strain of HIV-1 isolate ENV_HV1LW, Swiss-Prot Q70626), where the cysteine amino acid residues in positions 598 and 604 have been replaced by serine amino acid residues. Immunodominant region refers to a peptide sequence that induces, in a great majority of cases (for example in at least 7 cases out of 10 approximately), a humoral and/or cellular response of the immune system directed against the region after immunization with a protein containing the sequence or with a peptide essentially consisting of the sequence.

In the present application, when reference is made to an immune response, without any other specific information, it is an immune response of a vertebrate, following immunization in vivo.

The invention makes reference to the target cells of a virus which are the cells into which the virus is capable of penetrating. The target cells of retroviruses are generally known. Viruses have the property of binding to the cells which they are capable of infecting. It is therefore optionally possible to test for, using routine experiments in vitro, the target cells of a virus studied.

The invention also makes reference to the cells of the host having a membrane receptor for a protein of the host. The cells of the host which have a receptor for a protein of said host are often known and, in the opposite case, it is possible, using routine experiments, to determine if a given protein binds to a certain type or cell. It is possible, for example, to use a radiolabelled protein and to determine if it binds to said cell type. It is also possible to test if the protein binds to a given membrane receptor using a cell line transfected with a gene expressing said membrane receptor.

The proteins of the host for which certain cells of the host possess a membrane receptor are mainly proteins belonging to the range of soluble protein mediators. This range includes proteins called, depending on the cases, hormones, growth factors or cytokines, although there is no distinct boundary between these various categories of mediators; see for example CAVAILLON J. M., Les Cytokines (Masson, Paris, 1966) Chapter 1, pages 1-3 and preface.

The linker fragment considered according to the invention have an overall hydrophilic character and is non or weakly immunogenic and flexible.

It is a synthetic linker and more particularly, it will be an oligopeptide linker.

As used herein, a "flexible" linker is one that lacks a substantially stable higher-order conformation in solution. Areas of local charge are to be avoided. In general, small, polar, and hydrophilic residues are preferred, and bulky and hydrophobic residues are undesirable. If the linker polypeptide includes charged residues, they will ordinarily be positioned so as to provide a net neutral charge within a small region of the polypeptide. It is therefore preferred to place a charged residue adjacent to a residue of opposite charge.

In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Cys, Pro, Leu, Ile, Lys, and Arg residues will be avoided, Cys residues due to their potential for formation of unwanted disulfide bonds, Pro residues due to their hydrophobicity and lack of flexibility, and Lys and Arg residues due to risk of possible immunogenicity.

A convenient linker may be represented by the sequence of SEQ ID NO 2 represented in FIG. 2C.

This linker fragment is included in the loop in substitution of wildtype residues.

The deleted wildtype oligopeptide may have or not the same length than the linker oligopeptide.

In a specific embodiment, the deleted wildtype oligopeptide will be shorter than the fragment linker.

In another specific embodiment, the deleted wildtype will be longer than the fragment linker.

In still another specific embodiment, they will have the same length.

Wildtype oligopeptides that may be advantageously replaced by a linker in accordance with the present invention are represented by SEQ ID NO 15 and SEQ ID NO 16 (FIG. 2D). These correspond respectively to amino acids to 599 to 610, and 593 to 610 of SEQ ID NO 1 as numbered in FIG. 2A, and to amino acids 61 to 72 and 55 to 79 of SEQ ID NO 14.

According to a specific embodiment, the modified polypeptide in accordance with the present invention includes furthermore at least one mutation in its immunodominant region.

The immunodominant regions of which it is desired to modify the antigenicity, in accordance with the invention, may be chosen from those which give in vitro a cross-reaction, of the B type and/or the T type, with a host protein and in particular with IL-2.

In the appended FIG. 2B, the peptide sequences of four regions of this region of gp41 550 to 572 (SEQ ID NO 3), 567 to 596 (SEQ ID NO 4), 585 to 615 (SEQ ID NO 5) and 623 to 658 (SEQ ID NO 6), are represented in which structural analogies and/or cross reactions were noted with IL-2. These regions are homologously found in the SEQ ID NO 14, and respectively correspond to the peptide sequences found in positions 12 to 34, 29 to 58, 47 to 77, and 85 to 120.

Accordingly, within another aspect of the invention, there is provided a modified polypeptide as disclosed here-above and including furthermore at least a mutation in its immunodominant region to prevent a cross reaction of the B type and/or the T type with a host protein and in particular with human IL-2.

Are particularly interesting modified polypeptides according to the invention including furthermore at least a mutation in one of the immunodominant region represented by the peptide sequence SEQ ID NO 3, SEQ ID NO 4, SEQ ID NO 5 and/or SEQ ID NO 6.

In the present application, "mutation" refers to any modification of a region (optionally reduced to a single amino acid residue) of a polypeptide, by physical means, chemical means (covalent or noncovalent modification) and/or biological means (mutations by substitution, deletion and/or insertion of one or more amino acids), leading to the modification of the functional potentials of the constituent amino acid(s) of said region, termed "mutated region". By way of example, it is possible to carry out mutations leading to the abolition, acquisition and/or modulation of the properties of disulfide bridges, hydrogen bonds, electrostatic interactions and/or hydrophobic interactions, the modification of the capacity of a protein to form a heterocomplex, or alternatively, in the case of an oligomeric protein, the modification of the state of oligomerization or of the stability of the oligomer.

Some of the mutations decisive to impact this change in the antigenicity are disclosed in U.S. Pat. No. 6,455,265 which teaching is hereby incorporated by reference herein in its entirety.

A modified polypeptide according to the instant invention is in particularly represented by the sequence SEQ ID NO 8 of FIG. 1. This modified polypeptide has been derived from SEQ ID NO 14, wherein the oligopeptide sequence from positions 599-610 has been replaced with a linker corresponding to SEQ ID NO 2 (FIG. 2C), and the oligopeptide sequence from positions 665-675 has been replaced by a His-Tag. In these sequences, an additional mutation has been carried-out in position 58 (numbering according to SEQ ID NO 14), wherein a tryptophan residue has been replaced by an aspartate amino acid residue.

Others polypeptide sequences illustrating the present invention are represented by SEQ ID NO 17, SEQ ID NO 18, SEQ ID NO 19 and SEQ ID NO 20 (FIGS. 4 and 5).

According to another particular embodiment of the instant invention the gp41 modified polypeptide may also include modification such as truncation of a part of the amino acid sequence at the N or C-terminal extremities.

In an advantageously embodiment, the gp41 modified polypeptide is truncated at the N-terminal extremity.

Without wishing to be bound by any theory, the inventors hypothesize that such polypeptide modifications allow to some C-peptide sequences not being, for instance totally or partially, masked, in particular at the C-terminal extremity, which is therefore more readily accessible to antibodies.

More particularly, the gp41 modified polypeptide is a N-truncated oligopeptide. The length of the deletion is of a size ranging from 8 to 15 amino acid residues numbered from SEQ ID NO 1.

More advantageously, the gp41 modified polypeptide is truncated of at least 10, in particular of at least 12 amino acid residues at the N-terminal position.

An illustrative polypeptide sequence exhibiting N-terminal truncation and a replacement in the loop sequence of a oligopeptide sequence by a linker (SEQ ID NO 2) in accordance with the instant invention, is in particular represented by the sequence SEQ ID NO 21 (FIG. 6).

According to another particular embodiment of the invention, it may be possible to include besides the loop modifications, carried-out to improve the solubility, and the modifications to improve the antigenicity of the gp41 polypeptide, additional modifications to improve solubility.

As a particular embodiment of such modifications, mention may be made of amino acid residue mutation, as for example changing the tryptophan residue in position 58 (numbering of SEQ ID NO 14) by a more hydrophilic amino acid residue, such as an aspartate.

Other similar mutations are illustrated by the gp41 modified polypeptides set forth in SEQ ID NO 17 and SEQ ID NO 19 wherein the tryptophan in position 124 in SEQ ID NO 17 and 130 in SEQ ID NO 19, that would correspond to the tryptophan in position 680 of SEQ ID NO 1 (not represented in this sequence), has been exchanged by an aspartate.

Such mutations are carried-out in the purpose of changing hydrophobic amino acid residues by more hydrophilic amino acid residues.

Other modifications to improve the solubility of the gp41 modified polypeptide may be deletion or insertion of amino acid residues.

As particular embodiment of such modifications, mention may be made of amino acid residues deletion, as for example deletion of amino acid residues tryptophan and leucine respectively in positions 122 and 123 of SEQ ID NO 17, and in positions 128 and 129 of SEQ ID NO 19 to give respectively the sequences set forth as SEQ ID NO 18 and SEQ ID NO 20.

Moreover, without departing of the ambit in the instant invention, the modified polypeptides in the accordance with the present invention may include additional modifications useful for laboratory experiments, such as fusion with a His-Tag or a fluorescent protein, as for example Green Fluorescent Protein.

Illustrative gp41 modified polypeptides according to the instant invention which carry additional modifications, as His-Tag, are set forth in SEQ ID NO 8, SEQ ID NO 17, SEQ ID NO 18, SEQ ID NO 19, SEQ ID NO 20 and, SEQ ID NO 21 (FIGS. 1, 4-6). The His-Tag has been added at the C-terminal extremity of those peptides.

To prepare the modified polypeptide according to the invention, it is possible to use any known methods of peptide synthesis or genetic engineering techniques, such as described in *Molecular cloning: a laboratory manual*, 3$^{rd}$ ed., Cold Spring Harbor Laboratory Press, Cold Spring Harbor, N.Y., 2001.

It is possible to isolate or to prepare a polynucleotide sequence encoding at least part of the envelopes gp41 of HIV-1 and, if desired, it is possible to introduce at this stage, into the nucleotide sequence, the linker and optionally the mutation which make it possible to obtain a mutated product of translation which constitutes the modified polypeptide.

It is also possible to directly synthesize a modified polynucleotide sequence comprising one or more mutations encoding the modified polypeptide. The mutated polynucleotide sequences thus obtained are introduced in a known manner into an appropriate vector which makes it possible to express said polypeptide, optionally in modified form. Such a vector is for example *E. Coli*, a baculovirus or a mammalian cell. It is also possible to carry out the mutation on an unmodified polypeptide obtained according to one of the preceding methods.

Accordingly, the present invention is also directed to polynucleotide molecules, including DNA and RNA molecules, that encode the modified polypeptides disclosed above.

The polynucleotides of the present invention include both single-stranded and double-stranded molecules. A representative DNA sequence is set forth in SEQ ID NO 7 of FIG. 1.

Additional DNA sequences encoding modified polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding modified polypeptides.

The subject of the invention is also the use of a modified polypeptide, as defined above, in the preparation of a vaccine composition for preventing the pathogenic effects related to the infection of a host by a retrovirus HIV-1.

Thus, the modified polypeptide obtained according to the invention can serve as immunogenic agent in order to induce, by immunization, the formation of antibodies which can be used in particular in the treatment of retroviral infections, and the invention therefore also relates to the antibodies obtained in response to the immunization of animals (including humans), in vivo with the aid of the vaccine agent containing a modified polypeptide as above-described.

The pharmaceutical compositions containing such antibodies also constitute one of the subjects of the invention.

It is known from the person skilled in the art that there are various strains of a HIV viruses, and therefore various homologous forms of gp41 proteins.

It is also known from the person skilled in the art that knowing various homologous sequences of a given peptide or a protein, it is possible to design consensus sequences of such peptide or protein that display the sequence of amino acid residues the most frequently present in such protein or peptide.

Consequently, it is not going beyond the scope of the instant invention to carrying similar loop engineering and the other disclosed modifications by adapting them to a particular gp41 protein isoform to modify or to a consensus sequence to modify.

The following non limiting examples illustrate the invention.

Example 1

Construction of gp41-Engineered Loop of SEQ ID NO 8 by Molecular Biology a) Design of the Oligonucleotide Primers The gp41-engineered loop was constructed by PCR. The amplification of the N-helix and introduction of the hydrophilic linker was carried out by using the oligonucleotide primer gp41-NdeI (SEQ ID NO 9): 5' GG AAT CCA CATATG CAG GCC AGA CAA TTA TTG 3', and the oligonucleotide primer gp41-Bam1IL (SEQ ID NO 10): 5'ACC GTT GGATCC ACCTCTACCTCCACT GCT ACC GTC AAT CCC CAG GAG CTG TTG ATC 3' (FIG. 7).

These oligonucleotide primers were designed to respectively introduce the sites for restriction enzymes NdeI and BamHI (twice underlined into the oligonucleotides primers sequences above). The sequences homologous to the gp41 gene in both oligonucleotide primers are written in italics. The oligonucleotide primer gp41-BamIL was also designed to introduce (1) the oligopeptide linker SGGRGGS (SEQ ID NO 2) to replace the deleted portion of the loop (corresponding to the once and twice underlined sequences) and (2) a mutation at position 58 (protein numbering SEQ ID NO 14), where a tryptophan has been replaced by an aspartate amino acid (bold triplet).

The amplification of the C-helix of gp41 protein was carried-out by PCR, using the oligonucleotide primer gp41-

Bam2IL (SEQ ID NO 11): 5' GG AAT CCA <u>GGATCC</u> AAT GCT AGT TGG AGT ATA AAA TCT CTG *GAA* 3', and the oligonucleotide prier gp41-XhoI (SEQ ID NO 12): 5' GCC CGG <u>CTCGAG</u> ATC TAA TTC CAA TAA TTC TTG TTC ATT *CTT TTC* 3' (FIG. 7). Those oligonucleotide primers were designed to respectively introduce the BamHI and the Xho1 enzyme sites restrictions (sequences twice underlined). The sequences homologous to the gp41 gene are written in italic in both primers.

b) Conditions of PCR

The gp41 modified polypeptide was amplified from the gp41 matrix (SEQ ID NO 13) by PCR using the above-described oligonucleotide primers. Plasmid was used at 0.5 µg/µl, primers were used at 10 µM each, and dNTP were used at 10 mM each. The amplification was conducted using the DNA polymerase DyNazyme from Finnzymes. The amplification was initiated with a denaturing step of 5 minutes at 94° C., following by 30 cycles, each comprising a one minute step at 94° C. (denaturing step), a one minute step at 60° C. (hybridization), and a one minute step at 72° C. (elongation), and the amplification was terminated by a last step of 10 minutes at 72° C.

The purified PCR products were digested by NdeI-BamHI for the N-helix amplification and by BamHI and XhoI for the C-helix amplification. The two purified NdeI-BamHI and BamHI-XhoI fragments were ligated into the NdeI-XhoI sites of pET21b vector (Novagen®) resulting in pET21b-gp41-engineered loop.

The introduction of the ligated fragment into the XhoI site of the pET21b plasmid results in addition of a His-Tag at the C-terminus of the gp41 modified polypeptides preceded by a glutamate and leucine amino acid residues (see SEQ ID NO 8) pET21b-gp41-engineered loop products were transformed in DH5a.

The complete nucleotide sequence of gp41 modified polypeptide (SEQ ID NO 8) was determined by Genome Express (Grenoble). No mutation was detected.

Example 2

Modified Polypeptide Reproduction in *E. coli* a) Transformation pET21b-gp41-engineered loop plasmid is transformed in expression *E. coli* strain (BL21(DE3)).

b) Expression Tests 6 cultures of *E. coli* strain BL21(DE3) carrying the pET21b-gp41-engineered loop plasmid were grown at 37° C. in Luria Broth until the optical density at 600 nm reached 0.6 (spectrophotometer Jasco V-530). The modified polypeptide was induced with 1 mM IPTG (isopropyl βD-thiogalactoside), and the culture continued for further 2 hours at 37° C. The gp41-engineered loop protein is expressed in *E. coli* as a 15 kDa protein specie.

Expression of proteins were controlled by separation by SDS-4-12% PAGE and immunoblotting with antibodies anti-His tag.

c) Production

1) Culture

One liter of culture of BL21 (DE3)/pET21b-gp41-engineered loop was grown in Luria Broth at 37° C. until the optical density at 600 nm reached the value of 6.0. The expression of gp41-engineered loop was induced by 1 mM IPTG, and the culture continued for a further 2 hours at 37° C. The culture was centrifuged (Centrifuge Beckman Coulter Avanti J20XP with rotor JLA 8-1000, 4000×g, 30 min, 4° C.) and the pellet was stored at −80° C.

2) Extraction of gp41 Modified Polypeptide

The pellet was resuspended with a sonication buffer (40 mL of Tris-HCl 50 mM pH8, NaCl 300 mM). Bacteria were disrupted by a 15 min sonication step on ice/ethanol (disintegrator UP200S amplitude 80%, coeff. 0.5). Then the suspension was centrifuged at 40 000×g during 30 min at 4° C. to separate the soluble proteins (supernatant) from the insoluble proteins (pellet) (Centrifuge Beckman Coulter Avanti J20XP with rotor JA20).

The gp41 modified polypeptide is soluble in the sonication supernatant in majority (80%).

d) Purification of gp41 Modified Polypeptide

The sonication supernatant (# 50 mL) was filtered through a 0.2-µm filter. The presence of 6 His at the C-terminal extremity allows a purification by affinity chromatography columns.

1) Affinity Chromatography

The affinity chromatography was conducted using an Akta FPLC (Fast-Pressure Liquid Chromatography, Amersham-Biosciences), and a Chelating Sepharose Fast Flow column (from Amersham-Pharmacia). The column was initially equilibrated with the passage of equilibration buffer A (Tris 50 mM pH8, NaCl 300 mM) (10 times the column volume).

Then 50 ml of sample containing gp41-engineered loop proteins were past through the column.

The contaminants were eluted in four steps with the passage of Buffer A comprising increasing amount of Buffer B (Tris 50 mM pH8, NaCl 300 mM, Imidazole 500 mM) in a volume corresponding to 10 times the column volume at each step (0, 20, 50 and 100 mM Imidazole). And finally the gp41 protein was eluted with the passage of 100% of Buffer B, in a volume corresponding to ten times the column volume.

The flow rate was set up at 8 mL/min and the collected fraction volume was 2 mL.

The presence of proteins was detected using an UV lamp and measuring of the absorbance at 280 nm.

The first four fractions were collected and mixed (8 mL at 0.2 mg/mL).

2) Dialysis

The gp41-engineered loop protein (8 mL in the buffer B (Tris 50 mM pH8, NaCl 300 mM, Imidazole 500 mM) was dialyzed three times (two analysis of 1 h 30 and one overnight) at 4° C. against 300 mL of Tris 50 mM pH8, NaCl 200 mM, Imidazole 200 mM. The resulting sample was centrifuged during 30 min at 30 000 g, 4° C.

From one liter of bacterial culture, 10 mL of purified gp41-engineered loop protein in Tris 50 mM pH8, NaCl 200 mM, Imidazole 200 mM at 0.2 mg/mL were obtained.

For the storage at −80° C., glycerol 5% was added and the purified protein was frozen in liquid nitrogen. At this step, the protein concentration was about 0.2 mg/mL.

Example 3 a) Determination of the Oligomeric State

Gel filtration with a separation between 3 000 and 600 000 Dalton was performed to determine the oligomeric state of the gp41-engineered loop protein.

The determination of the oligomeric state was conducted using a Fast Performance Liquid Chromatography (System BioLogic, Bio-Rad), with a analytic chromatography column Superdex 200 HR 10/30 Amersham-pharmacia.

The column was equilibrated with 50 ml of Buffer A (Tris 50 mM pH8, NaCl 200 mM), then 250 ml of sample containing gp41-engineered loop protein (corresponding to 500 μg of gp41-engineered loop protein) were passed through the column.

The proteins were therefore eluted using 30 ml of buffer A at a flow rate of 0.25 mL/min. The collected volume fraction was 2 mL. The proteins were detected using UV lamp and measuring of the absorbance at 280 nm.

The resulting chromatogram (FIG. 8) indicated that the gp41-engineered loop protein construct was produced in a soluble and stable trimeric form at 0.2 mg/mL.

The differences between the consensus sequence of the gp41 ectodomain and the gp41-engineered loop were of 13%. Among the 18 amino acids constituting the ectodomain, 6 were different and 12 were removed. The ectodomain of the gp41 protein represents 71% of the entire gp41 sequence.

TABLE I

| Summary of results | |
|---|---|
| Construct | gp41 modified polypeptide |
| Expression system | *E. coli* |
| Yield per liter of culture | 10 mL of purified protein at 0.2 mg/mL |
| Expressed as | Soluble fraction |
| Purity after refolding | >97% |
| pH behaviour | Soluble at pH superior or equal to 7 |
| Chromatography steps | Purification onto affinity chromatography |
| Oligomeric state | Trimeric soluble at 0.2 mg/mL |

The invention claimed is:

1. A modified human immunodeficiency virus type 1 (HIV-1) gp41 polypeptide, comprising a full-length sequence selected from the group consisting of the sequences set forth in SEQ ID NOs: 8 and 17-21.

2. An immunogenic composition containing as an active ingredient a modified polypeptide as defined in claim 1.

3. A modified human immunodeficiency virus type 1 (HIV-1) gp41 polypeptide, comprising amino acid residues 1-108 of SEQ ID NO: 17.

4. An immunogenic composition containing as an active ingredient a modified polypeptide as defined in claim 3.

5. A modified human immunodeficiency virus type 1 (HIV-1) gp41 polypeptide, comprising the sequence set forth in SEQ ID NO:1, wherein:
   amino acids 54-78 are replaced by a linker consisting of the sequence set forth in SEQ ID NO:2; and
   amino acids 126-139 are deleted.

6. An immunogenic composition containing as an active ingredient a modified polypeptide as defined in claim 5.

* * * * *

SEQUENCE LISTING

```
<160> NUMBER OF SEQ ID NOS: 21

<210> SEQ ID NO 1
<211> LENGTH: 140
<212> TYPE: PRT
<213> ORGANISM: Artificial Sequence
<220> FEATURE:
<223> OTHER INFORMATION: Synthetic

<400> SEQUENCE: 1

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
    50                  55                  60

Cys Thr Thr Ala Val Pro Trp Asn Ala Ser Trp Ser Asn Lys Ser Leu
65                  70                  75                  80

Glu Gln Ile Trp Asn Asn Met Thr Trp Met Glu Trp Asp Arg Glu Ile
                85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn Trp Leu
    130                 135                 140

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ser Gly Gly Arg Gly Gly Ser
1               5

<210> SEQ ID NO 3
<211> LENGTH: 23
<212> TYPE: PRT
<213> ORGANISM: Artificial Sequence
<220> FEATURE:
<223> OTHER INFORMATION: Synthetic
```

<400> SEQUENCE: 3

Gln Gln Gln Asn Asn Leu Leu Arg Ala Ile Glu Ala Gln Gln His Leu
1               5                   10                  15

Leu Gln Leu Thr Val Trp Gly
            20

<210> SEQ ID NO 4
<211> LENGTH: 30
<212> TYPE: PRT
<213> ORGANISM: Artificial Sequence
<220> FEATURE:
<223> OTHER INFORMATION: Synthetic

<400> SEQUENCE: 4

Gln Leu Thr Val Trp Gly Ile Lys Gln Leu Gln Ala Arg Ile Leu Ala
1               5                   10                  15

Val Glu Arg Tyr Leu Lys Asp Gln Gln Leu Leu Gly Ile Trp
            20                  25                  30

<210> SEQ ID NO 5
<211> LENGTH: 31
<212> TYPE: PRT
<213> ORGANISM: Artificial sequence
<220> FEATURE:
<223> OTHER INFORMATION: synthetic

<400> SEQUENCE: 5

Arg Tyr Leu Lys Asp Gln Gln Leu Leu Gly Ile Trp Gly Cys Ser Gly
1               5                   10                  15

Lys Leu Ile Cys Thr Thr Ala Val Pro Trp Asn Ala Ser Trp Ser
            20                  25                  30

<210> SEQ ID NO 6
<211> LENGTH: 36
<212> TYPE: PRT
<213> ORGANISM: Artificial sequence
<220> FEATURE:
<223> OTHER INFORMATION: Synthetic

<400> SEQUENCE: 6

Trp Asn Asn Met Thr Trp Met Glu Trp Asp Arg Glu Ile Asn Asn Tyr
1               5                   10                  15

Thr Ser Leu Ile His Ser Leu Ile Glu Glu Ser Gln Asn Gln Gln Glu
            20                  25                  30

Lys Asn Glu Gln
        35

<210> SEQ ID NO 7
<211> LENGTH: 390
<212> TYPE: DNA
<213> ORGANISM: Artificial sequence
<220> FEATURE:
<223> OTHER INFORMATION: Gp41

<400> SEQUENCE: 7
atgcaggcca gacaattatt gtctggtata gtgcagcagc agaacaattt cctgagggct     60
attgaggcgc aacagcatct gttgcaactc acagtctggg gcatcaagca gctccaggca    120
agaatcctgg ctgtggaaag atacctaaag gatcaacagc tcctggggat tgacggtagc    180
agtggaggta gaggtggatc caatgctagt tggagtaata atctctgga acagatttgg    240 aatcacacga cctggatgga gtgggacaga gaaattaaca attacacaag cttaatacac    300

```
tccttaattg aagaatcgca aaaccagcaa gaaaagaatg aacaagaatt attggaatta    360
gatctcgagc accaccacca ccaccactga                                    390
```

<210> SEQ ID NO 8
<211> LENGTH: 129
<212> TYPE: PRT
<213> ORGANISM: Artificial sequence
<220> FEATURE:
<223> OTHER INFORMATION: Gp41

<400> SEQUENCE: 8

```
Met Gln Ala Arg Gln Leu Leu Ser Gly Ile Val Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Leu Gly Ile Asp Gly Ser Ser Gly Gly Arg
    50                  55                  60

Gly Gly Ser Asn Ala Ser Trp Ser Asn Lys Ser Leu Glu Gln Ile Trp
65                  70                  75                  80

Asn His Thr Thr Trp Met Glu Trp Asp Arg Glu Ile Asn Asn Tyr Thr
                85                  90                  95

Ser Leu Ile His Ser Leu Ile Glu Glu Ser Gln Asn Gln Gln Glu Lys
            100                 105                 110

Asn Glu Gln Glu Leu Leu Glu Leu Asp Leu His His His His His
        115                 120                 125

His
```

<210> SEQ ID NO 9
<211> LENGTH: 32
<212> TYPE: DNA
<213> ORGANISM: Artificial sequence
<220> FEATURE:
<223> OTHER INFORMATION: Primer

<400> SEQUENCE: 9

```
ggaatccaca tatgcaggcc agacaattat tg                                 32
```

<210> SEQ ID NO 10
<211> LENGTH: 57
<212> TYPE: DNA
<213> ORGANISM: Artificial Sequence
<220> FEATURE:
<223> OTHER INFORMATION: Primer

<400> SEQUENCE: 10

```
accgttggat ccacctctac ctccactgct accgtcaatc cccaggagvt gttgatc      57
```

<210> SEQ ID NO 11
<211> LENGTH: 44
<212> TYPE: DNA
<213> ORGANISM: Artificial Sequence
<220> FEATURE:
<223> OTHER INFORMATION: Primer

<400> SEQUENCE: 11

```
ggaatccagg atccaatgct agttggagta ataaatctct ggaa                    44
```

<210> SEQ ID NO 12
<211> LENGTH: 45
<212> TYPE: DNA

```
<213> ORGANISM: Artificial Sequence
<220> FEATURE:
<223> OTHER INFORMATION: Primer

<400> SEQUENCE: 12
gcccggctcg agatctaatt ccaataattc ttgttcattc ttttc            45

<210> SEQ ID NO 13
<211> LENGTH: 411
<212> TYPE: DNA
<213> ORGANISM: Artificial Sequence
<220> FEATURE:
<223> OTHER INFORMATION: GP41

<400> SEQUENCE: 13
gtacaggcca gacaattatt gtctggtata gtgcagcagc agaacaattt gctgagggct    60
attgaggcgc aacagcatct gttgcaactc acagtctggg gcatcaagca gctccaggca   120
agaatcctgg ctgtggaaag atacctaaag gatcaacagc tcctggggat ttggggtagc   180
tctggaaaac tcattagcac cactgctgtg ccttggaatg ctagttggag taataaatct   240
ctggaacaga tttggaatca cacgacctgg atggagtggg acagagaaat taacaattac   300
acaagcttaa tacactcctt aattgaagaa tcgcaaaacc agcaagaaaa gaatgaacaa   360
gaattattgg aattagataa atgggcaagt ttgtggaatt ggtttaacat a            411

<210> SEQ ID NO 14
<211> LENGTH: 137
<212> TYPE: PRT
<213> ORGANISM: Artificial Sequence
<220> FEATURE:
<223> OTHER INFORMATION: GP41

<400> SEQUENCE: 14

Val Gln Ala Arg Gln Leu Leu Ser Gly Ile Val Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Leu Gly Ile Trp Gly Ser Ser Gly Lys Leu
    50                  55                  60

Ile Ser Thr Thr Ala Val Pro Trp Asn Ala Ser Trp Ser Asn Lys Ser
65                  70                  75                  80

Leu Glu Gln Ile Trp Asn His Thr Thr Trp Met Glu Trp Asp Arg Glu
                85                  90                  95

Ile Asn Asn Tyr Thr Ser Leu Ile His Ser Leu Ile Glu Glu Ser Gln
            100                 105                 110

Asn Gln Gln Glu Lys Asn Glu Gln Glu Leu Leu Glu Leu Asp Lys Trp
        115                 120                 125

Ala Ser Leu Trp Asn Trp Phe Asn Ile
    130                 135

<210> SEQ ID NO 15
<211> LENGTH: 13
<212> TYPE: PRT
<213> ORGANISM: Artificial Sequence
<220> FEATURE:
<223> OTHER INFORMATION: Synthetic

<400> SEQUENCE: 15

Cys Ser Gly Lys Leu Ile Cys Thr Thr Ala Val Pro Trp
```

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

```
Leu Gly Ile Trp Gly Cys Ser Gly Lys Leu Ile Cys Thr Thr Ala Val
1               5                   10                  15
Pro Trp Asn Ala Ser Trp Ser Asn Lys
            20                  25
```

<210> SEQ ID NO 17
<211> LENGTH: 130
<212> TYPE: PRT
<213> ORGANISM: Artificial Sequence
<220> FEATURE:
<223> OTHER INFORMATION: Synthetic

<400> SEQUENCE: 17

```
Met Gln Ala Arg Gln Leu Leu Ser Gly Ile Val Gln Gln Gln Asn Asn
1               5                   10                  15
Leu Leu Arg Ala Ile Glu Ala Gln Gln His Leu Leu Gln Leu Thr Val
            20                  25                  30
Trp Gly Ile Lys Gln Leu Gln Ala Arg Ile Leu Ala Val Glu Arg Tyr
        35                  40                  45
Leu Lys Asp Gln Gln Leu Ser Gly Gly Arg Gly Gly Ser Ser Leu Glu
    50                  55                  60
Gln Ile Trp Asn His Thr Thr Trp Met Glu Trp Asp Arg Glu Ile Asn
65                  70                  75                  80
Asn Tyr Thr Ser Leu Ile His Ser Leu Ile Glu Glu Ser Gln Asn Gln
                85                  90                  95
Gln Glu Lys Asn Glu Gln Glu Leu Leu Glu Leu Asp Lys Trp Ala Ser
            100                 105                 110
Leu Trp Asn Trp Phe Asn Ile Thr Asn Trp Leu Asp His His His His
        115                 120                 125
His His
    130
```

<210> SEQ ID NO 18
<211> LENGTH: 128
<212> TYPE: PRT
<213> ORGANISM: Artificial Sequence
<220> FEATURE:
<223> OTHER INFORMATION: Synthetic

<400> SEQUENCE: 18

```
Met Gln Ala Arg Gln Leu Leu Ser Gly Ile Val Gln Gln Gln Asn Asn
1               5                   10                  15
Leu Leu Arg Ala Ile Glu Ala Gln Gln His Leu Leu Gln Leu Thr Val
            20                  25                  30
Trp Gly Ile Lys Gln Leu Gln Ala Arg Ile Leu Ala Val Glu Arg Tyr
        35                  40                  45
Leu Lys Asp Gln Gln Leu Ser Gly Gly Arg Gly Gly Ser Ser Leu Glu
    50                  55                  60
Gln Ile Trp Asn His Thr Thr Trp Met Glu Trp Asp Arg Glu Ile Asn
65                  70                  75                  80
```

```
Asn Tyr Thr Ser Leu Ile His Ser Leu Ile Glu Glu Ser Gln Asn Gln
                85                  90                  95

Gln Glu Lys Asn Glu Gln Glu Leu Leu Glu Leu Asp Lys Trp Ala Ser
            100                 105                 110

Leu Trp Asn Trp Phe Asn Ile Thr Asn Asp His His His His His His
        115                 120                 125

<210> SEQ ID NO 19
<211> LENGTH: 136
<212> TYPE: PRT
<213> ORGANISM: Artificial Sequence
<220> FEATURE:
<223> OTHER INFORMATION: Synthetic

<400> SEQUENCE: 19

Met Gln Ala Arg Gln Leu Leu Ser Gly Ile Val Gln Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Leu Gly Ile Trp Gly Ser Ser Gly Gly Arg
    50                  55                  60

Gly Gly Ser Ser Leu Glu Gln Ile Trp Asn His Thr Thr Trp Met Glu
65                  70                  75                  80

Trp Asp Arg Glu Ile Asn Asn Tyr Thr Ser Leu Ile His Ser Leu Ile
                85                  90                  95

Glu Glu Ser Gln Asn Gln Gln Glu Lys Asn Glu Gln Glu Leu Leu Glu
            100                 105                 110

Leu Asp Lys Trp Ala Ser Leu Trp Asn Trp Phe Asn Ile Thr Asn Trp
        115                 120                 125

Leu Asp His His His His His His
    130                 135

<210> SEQ ID NO 20
<211> LENGTH: 134
<212> TYPE: PRT
<213> ORGANISM: Artificial Sequence
<220> FEATURE:
<223> OTHER INFORMATION: Synthetic

<400> SEQUENCE: 20

Met Gln Ala Arg Gln Leu Leu Ser Gly Ile Val Gln Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Leu Gly Ile Trp Gly Ser Ser Gly Gly Arg
    50                  55                  60

Gly Gly Ser Ser Leu Glu Gln Ile Trp Asn His Thr Thr Trp Met Glu
65                  70                  75                  80

Trp Asp Arg Glu Ile Asn Asn Tyr Thr Ser Leu Ile His Ser Leu Ile
                85                  90                  95

Glu Glu Ser Gln Asn Gln Gln Glu Lys Asn Glu Gln Glu Leu Leu Glu
            100                 105                 110

Leu Asp Lys Trp Ala Ser Leu Trp Asn Trp Phe Asn Ile Thr Asn Asp
        115                 120                 125
```

```
<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Met Leu Leu Arg Ala Ile Glu Ala Gln Gln His Leu Leu Gln Leu Thr
1               5                   10                  15

Val Trp Gly Ile Lys Gln Leu Gln Ala Arg Ile Leu Ala Val Glu Arg
            20                  25                  30

Tyr Leu Lys Asp Gln Gln Leu Ser Gly Gly Arg Gly Gly Ser Ser Leu
        35                  40                  45

Glu Gln Ile Trp Asn His Thr Thr Trp Met Glu Trp Asp Arg Glu Ile
    50                  55                  60

Asn Asn Tyr Thr Ser Leu Ile His Ser Leu Ile Glu Glu Ser Gln Asn
65                  70                  75                  80

Gln Gln Glu Lys Asn Glu Gln Glu Leu Leu Glu Leu Asp Lys Trp Ala
                85                  90                  95

Ser Leu Trp Asn Trp Phe Asn Ile Thr Asn Trp Leu Asp His His His
            100                 105                 110

His His His
        115
```